US010031125B2

(12) United States Patent
Koo et al.

(10) Patent No.: US 10,031,125 B2
(45) Date of Patent: Jul. 24, 2018

(54) DIAGNOSIS AND TREATMENT OF INVASIVE ASPERGILLOSIS

(71) Applicants: THE BRIGHAM AND WOMEN'S HOSPITAL, INC., Boston, MA (US); THE CHARLES STARK DRAPER LABORATORY, INC., Cambridge, MA (US)

(72) Inventors: Sophia Koo, Brookline, MA (US); Horatio R. Thomas, Cambridge, MA (US); James Constantine Comolli, Boxborough, MA (US); Preshious Rearden, Melrose, MA (US); Lindsey R. Baden, Brookline, MA (US); Francisco M. Marty, Chestnut Hill, MA (US)

(73) Assignees: The Brigham and Women's Hospital, Inc., Boston, MA (US); The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 14/426,678

(22) PCT Filed: Sep. 6, 2013

(86) PCT No.: PCT/US2013/058560
§ 371 (c)(1),
(2) Date: Mar. 6, 2015

(87) PCT Pub. No.: WO2014/039856
PCT Pub. Date: Mar. 13, 2014

(65) Prior Publication Data
US 2015/0233895 A1 Aug. 20, 2015

Related U.S. Application Data

(60) Provisional application No. 61/698,155, filed on Sep. 7, 2012.

(51) Int. Cl.
G01N 33/497 (2006.01)
C12Q 1/02 (2006.01)
C12Q 1/04 (2006.01)
A61K 31/7048 (2006.01)
A61K 31/496 (2006.01)
A61K 31/513 (2006.01)
A61K 31/427 (2006.01)
A61K 38/12 (2006.01)

(52) U.S. Cl.
CPC ......... G01N 33/497 (2013.01); A61K 31/427 (2013.01); A61K 31/496 (2013.01); A61K 31/513 (2013.01); A61K 31/7048 (2013.01); A61K 38/12 (2013.01); C12Q 1/025 (2013.01); C12Q 1/04 (2013.01); G01N 2033/4977 (2013.01)

(58) Field of Classification Search
CPC ................................. G01N 33/497; C12Q 1/04
See application file for complete search history.

(56) References Cited

U.S. PATENT DOCUMENTS

| 7,019,291 | B2 | 3/2006 | Miller et al. |
| 7,605,367 | B2 | 10/2009 | Miller et al. |
| 8,481,789 | B2 * | 7/2013 | Mane ................. A23L 1/22628 435/148 |
| 2004/0092583 | A1 | 5/2004 | Shanahan-Prendergast |
| 2007/0003996 | A1 | 1/2007 | Hitt et al. |
| 2009/0078865 | A1 | 3/2009 | Zapata et al. |
| 2010/0291617 | A1 | 11/2010 | Trevejo et al. |
| 2013/0168548 | A1 | 7/2013 | Wang et al. |

OTHER PUBLICATIONS

Takeuchi et al. Surf Interface Anal. Mar. 2012, 44, pp. 694-698.*
Jelen et al. Journal of Agricultural and Food Chemistry, 2005, 53, pp. 1678-1683.*
Phillips et al. Caner Biomarkers, 2007, 3, pp. 95-109.*
International Search Report and Written Opinion dated Aug. 26, 2015 in international application No. PCT/US2015/34182, 10 pgs.
Baddley et al., "Patterns of susceptibility of Aspergillus isolates recovered from patients enrolled in the Transplant-Associated Infection Surveillance Network," J Clin Microbiol., Oct. 2009;47(10):3271-5.
Davis et al., "Spore biomarker detection using a MEMS differential mobility spectrometer," In: 12th International Conference on Transducers, Solid-State Sensors, Actuators and Microsystems; 2003: p. 1233-8 vol. 2.
Fong et al., "Automated peak detection and matching algorithm for gas chromatography-differential mobility spectrometry," Anal Chem., Mar. 1, 2011;83(5):1537-46 (Author Manuscript).
Kanu et al., "Ion mobility-mass spectrometry," J Mass Spectrom., Jan. 2008;43(1):1-22.
Kolakowski and Mester, "Review of applications of high-field asymmetric waveform ion mobility spectrometry (FAIMS) and differential mobility spectrometry (DMS)," Analyst., Sep. 2007;132(9):842-64.
Koo et al., "An Aspergillus fumigatus (AF)-specific Breath Volatile Organic Compound (VOC) Profile is Diagnostic of Invasive Aspergillosis (IA)," 53$^{rd}$ ICAAC, Sep. 10-13, 2013, 3 pages.
Krebs et al., "Detection of Biological and Chemical Agents Using Differential Mobility Spectrometry (DMS) Technology," Sensors Journal, IEEE 2005 5(4):696-703.
Luong et al., "Gas chromatography with state-of-the-art micromachined differential mobility detection: operation and industrial applications," J Chromatogr Sci., May-Jun. 2006;44(5):276-86.
Marr et al., Treatment and prevention of invasive aspergillosis, Up-To-Date (topic updated on Oct. 18, 2012; literature review Aug. 2013: available at http://www.uptodate.com/contents/treatment-and-prevention-of-invasive-aspergillosis?topicKey=ID%2F2459&elapsedTimeMs=7&view=print&displayedView=full, 18 pages).

(Continued)

Primary Examiner — Vera Afremova
(74) Attorney, Agent, or Firm — Fish & Richardson P.C.

(57) ABSTRACT

Methods for diagnosing, treating, and monitoring the treatment of invasive aspergillosis (IA) are described. The methods can include detecting the presence of one or more volatile organic compounds (VOCs) in the breath of subjects suspected of having IA.

23 Claims, 12 Drawing Sheets

(56) References Cited

OTHER PUBLICATIONS

Merrick, "Characterization of Human Expired Breath by Solid Phase Microextraction and Analysis Using Gas Chromatography-Mass Spectrometry and Differential Mobility Spectrometry," Thesis Harvard—MIT Division of Health Science and Technology, Aug. 10, 2005, 95 pages.
McDonagh et al., "Sub-telomere directed gene expression during initiation of invasive aspergillosis," PLoS Pathog., Sep. 12, 2008;4(9):e1000154, 21 pages.
Milroy et al., "Aspergillosis of the nose and paranasal sinuses," J Clin Pathol., Feb. 1989;42(2):123-7.
Nazarov et al., "Pressure effects in differential mobility spectrometry," Anal Chem., Nov. 15, 2006;78(22):7697-706.
Pontecorvo et al., "The genetics of Aspergillus nidulans," Adv Genet. 1953;5:141-238.
Shnayderman et al, "Species-specific bacteria identification using differential mobility spectrometry and bioinformatics pattern recognition," Anal Chem., Sep. 15, 2005;77(18):5930-7.
Walsh et al., "Treatment of aspergillosis: clinical practice guidelines of the Infectious Diseases Society of America," Clin Infect Dis., Feb. 1, 2008;46(3):327-60.
K.wak and Preti, "Volatile Disease Biomarkers in Breath: A Critique," Current Pharmaceutical Biotechnology, 2011, 12(7): 1067-1074.
Lin et al., "Identification of Unique Volatile Compounds of Aspergillus fumigatus for Potential Diagnostic Breath Test by HSSPME and GC-MS," J. Immunol. Tech. Infect. Dis., 2013, 2(3): 1-4.
Abstractonline.com [online] "Final Program 52nd Interscience Conference on Antimicrobial Agents and Chemotherapy Sep. 9-12, 2012," Sep. 9-12, 2012, [retrieved on Mar. 24, 2016]. Retrieved from the internet: URL:http://www.asm.org/images/ICAAC 2012 FinalProgram.Web4a.pdf, 330 pages.
Abstractonline.com [online] Oasis Product Development Team, "Online Program Planner for the 52nd ICACC—Sep. 9-12—San Francisco," Sep. 9-12, 2012, [retrieved on Mar. 24, 2016]. Retrieved from the internet: URL:http://www.abstractsonline.com/plan/start.aspx?mkey=%7B6B114AID-85A4-4054-A83B-04D8B9B8749F%7D, 2 pages.
Abstractonline.com [online] S. Koo et.al, "Breath Volatile organic Compound (VOC) Profiles for the Diagnosis of Invasive Aspergillosis (IA)," Online Meeting Planner for the 52nd Interscience Conference on Antimicrobial Agents and Chemotherapy (ICACC), Sep. 9-12, 2012, Aug. 9, 2012, [Retrieved on Mar. 24, 2016]. Retrieved from the internet: URL:http://www.abstractsonline.com/Plan/ViewAbstract.aspx?sKey=50e8c5eb-47e8-4e58-ed2-720d86b384f9&cKey=4920b27b-9cdd-4db3-822d-69b73708fc7c&mKey=%7b6B114A1D-85A4-4054-A83B-04D8B9B8749F%7d., 4 pages.
Bhandari et al., "Determining the limits and cofounders for the 2-penty1 furan breath test by gas chromatography/mass spectrometry," Journal of Chromatography B: Biomedical Sciences & Applications, 2011, 879(26): 2815-2820.
Chambers et al., "Novel diagnostics: progress toward a breath test for invasive Aspergillus fumigatus." Medical Mycology, 2011, 49(S1): S54-S61.
De Heer et al., "Electronic Nose Technology for Detection of Invasive Pulmonary Aspergillosis in Prolonged Chemotherapy-Induced Neutropenia: a Proof-of-Principle Study," Journal of Clinical Microbiology, Mar. 5, 2013, 51(5): 1490-1495.
Extended European Search Report in International Application No. PCT/US2013058560, dated Apr. 7, 2016, 9 pages.
Gao et al., "Determination of unique microbial volatile organic compounds produced by five Aspergillus species commonly found in problem buildings," AIHAJ: A Journal for the Science of Occupational and Environmental Health and Safety, 202, 62(2): 135-140.
Heddergott et al., "The Volatome of Apergillus fumigatus," Eukaryotic Cell, Aug. 2014, 13(8): 1014-1025.

International Preliminary Report on Patentability in International Application No. PCT/US2013/058560, dated Mar. 10, 2015, 13 pages.
Koo et al., "A Breath Fungal Secondary Metabolite Signature to Diagnose Invasive Aspergillosis," Clinical Infectious Diseases, Dec. 15, 2014, 59(12): 1733-1740.
Purkhart et al., "Chronic intestinal Mycobacteria infection: discrimination via VOC analysis in exhaled breath and headspace of feces using differential ion mobility spectrometry," Journal of Breath Research, 5(2), 2011, p. 027103.
U.S. Appl. No. 61/698,155, filed Sep. 7, 2012, Koo et al.
Balajee et al., "Molecular identification of Aspergillus species collected for the Transplant-Associated Infection Surveillance Network," J Clin Microbiol., Oct. 2009. 47: 3138-3141.
Bazemore et al., Biomedically important pathogenic fungi detection with volatile biomarkers, Journal of Breath Research, 2012, 6:016002.
Brakhage "Regulation of fungal secondary metabolism," Nature Reviews Microbiology, Jan. 2013, 11:21-32.
Cane and Kang, "Aristolochene synthase: purification, molecular cloning, high-level expression in Escherichia coli, and characterization of the Aspergillus terreus cyclase," Archives of Biochemistry and Biophysics, Apr. 2000, 376:354-364.
Chambers et al., "Novel diagnostics: progress toward a breath test for invasive Aspergillus fumigatus," Med Mycol., 2011, 49: S54-S61.
Chou et al., "Study of the chemical composition, antioxidant activity and anti-inflammatory activity of essential oil from Vetiveria zizanioides," Food Chem., Sep. 2012, 134(1):262-268.
De Pauw et al., "Revised definitions of invasive fungal disease from the European Organization for Research and Treatment of Cancer/Invasive Fungal Infections Cooperative Group and the National Institute of Allergy and Infectious Diseases Mycoses Study Group (EORTC/MSG) Consensus Group," Clin Infect Dis., 2008, 46:1813-1821.
Fiedler et al., "Detection of microbial volatile organic compounds (MVOCs) produced by moulds on various materials," Int J Hyg Environ Health, 2001, 204:111-121.
Frisvad et al., "Metabolomics of Aspergillus fumigatus," Med Mycol., 2009:47: S53-S71.
Hope et al., "Laboratory diagnosis of invasive aspergillosis." Lancet Infect Dis., Oct. 2005, 5:609-622.
International Preliminary Report on Patentability in International Application No. PCT/US2015/034182, dated Dec. 6, 2016, 8 pages.
Keller et al., "Fungal secondary metabolism—from biochemistry to genomics," Nat Rev Microbiol., Dec. 2005, 3:937-947.
Koo et al., "Diagnostic performance of the (1→3)-beta-D-glucan assay for invasive fungal disease," Clin Infect Dis., Dec. 2009, 49(11):1650-1659.
Kramer and Abraham, "Volatile sesquiterpenes from fungi: what are they good for?," Phytochemistry Reviews, 2012, 11:15-37.
Kwak and Preti, "Volatile disease biomarkers in breath: a critique," Curr Pharm Biotechnol., Jul. 2011,12(7):1067-1074.
Lin et al., "The fumagillin biosynthetic gene cluster in Aspergillus fumigatus encodes a cryptic terpene cyclase involved in the formation of β-trans-bergamotene," Journal of the American Chemical Society, Mar. 2013, 135:4616-4619.
Neofytos et al., "Epidemiology and outcome of invasive fungal infection in adult hematopoietic stem cell transplant recipients: analysis of Multicenter Prospective Antifungal Therapy (PATH) Alliance registry," Clin Infect Dis., Feb. 1, 2009, 48(3):265-273.
Pappas et al., "Invasive fungal infections among organ transplant recipients: results of the Transplant-Associated Infection Surveillance Network (TRANSNET)," Clinical Infectious Diseases, 2010, 50:1101-1111.
Perfect et al., "The impact of culture isolation of Aspergillus species: a hospital-based survey of aspergillosis." Clin Infect Dis., 2001, 33:1824-1833.
Pfeiffer CD, Fine JP, Safdar N. Diagnosis of invasive aspergillosis using a galactomannan assay: a meta-analysis. Clin Infect Dis. 2006;42:1417-1427.

(56) References Cited

OTHER PUBLICATIONS

Rath et al., "Differentiation of Aspergillus ustus Strains by Random Amplification of Polymorphic DNA," Journal of Clinical Microbiology, Jun. 2002, 40: 2231-2233.
Reichenberger et al., "Diagnostic yield of bronchoscopy in histologically proven invasive pulmonary aspergillosis." Bone Marrow Transplant, 1999, 24:1195-1199.
Sethi et al., "Clinical application of volatile organic compound analysis for detecting infectious diseases," Clinical Microbiology Reviews, Jul. 2013, 26:462-475.
Syhre et al., "Investigation into the production of 2-Pentylfuran by Aspergillus fumigatus and other respiratory pathogens in vitro and human breath samples," Med Mycol., 2008, 46:209-215.
Varga et al., "*Aspergillus calidoustus* sp. nov., causative agent of human infections previously assigned to Aspergillus ustus," Eukaryot Cell., 2008, 7: 630-638.

* cited by examiner

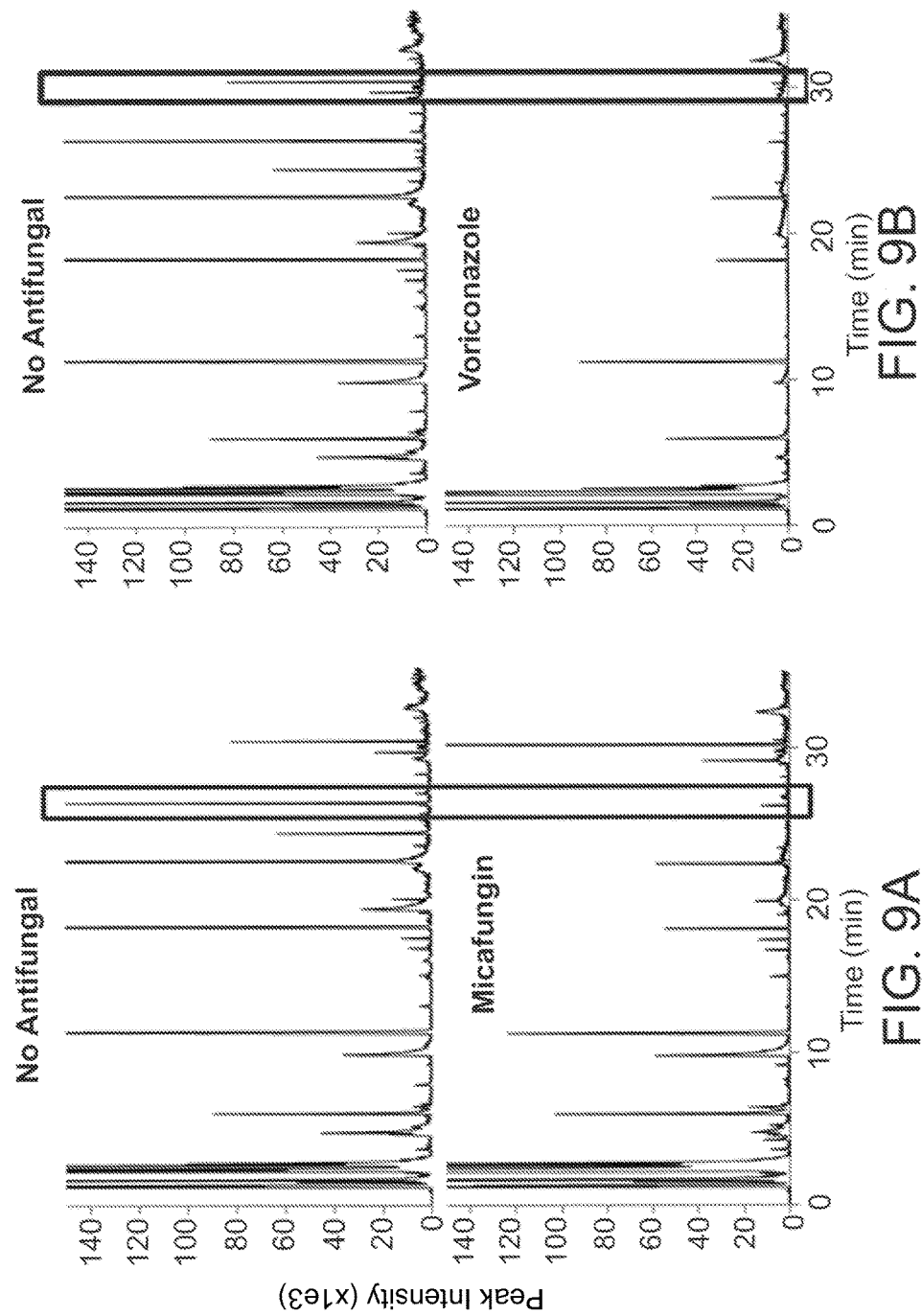

US 10,031,125 B2

DIAGNOSIS AND TREATMENT OF INVASIVE ASPERGILLOSIS

CLAIM OF PRIORITY

This application is a U.S. National Phase Application under 35 U.S.C. § 371 of International Patent Application No. PCT/US2013/058560, filed on Sep. 6, 2013, which claims the benefit of U.S. Provisional Application Ser. No. 61/698,155, filed on Sep. 7, 2012. The entire contents of the foregoing are incorporated herein by reference.

FEDERALLY SPONSORED RESEARCH OR DEVELOPMENT

This invention was made with Government support under Grants No. R21AI085454, K23AI097225 and 8UL1TR000170 awarded by the National Institutes of Health. The Government has certain rights in the invention.

TECHNICAL FIELD

Provided herein are methods for diagnosing, treating, and monitoring the treatment of invasive aspergillosis (IA). The methods can include detecting the presence of one or more volatile organic compounds (VOCs) in the breath of subjects suspected of having IA.

BACKGROUND

IA is a common, rapidly progressive, highly morbid, and frequently fatal infection in immunocompromised patients, especially in patients with chemotherapy-induced neutropenia or who are immunosuppressed as a result of receiving glucocorticoid treatment for graft-versus-host disease (GVHD). Timely diagnosis with prompt initiation of appropriate antifungal therapy improves clinical outcomes. Unfortunately, clinical and radiographic manifestations are nonspecific, and standard culture and antigen diagnostic approaches lack sensitivity and specificity for TA. Definitive diagnosis still relies on biopsy, which is often unacceptably morbid and frequently uninformative in these debilitated patients.

SUMMARY

As described herein, the present inventors have (1) identified a unique, species-specific profile of volatile organic compounds (VOCs) produced by *Aspergillus fumigatus, A. terreus, A. calidoustus*, and other pathogenic fungi in vitro that can be used to distinguish pathogenic fungal species from each other, (2) demonstrated that differential mobility spectrometry (DMS) can be used for the rapid discrimination between fungal species using pattern-based detection of these species-specific VOC profiles, and (3) accurately identified patients with invasive aspergillosis (IA) via direct detection of a pattern of *A. fumigatus* VOCs in their breath, including a combination of farnesene, beta-vatirenene, and cis-geranylacetone.

Thus in a first aspect, the invention provides methods for diagnosing a subject with invasive aspergillosis (IA). The methods include obtaining a sample comprising breath of a subject or headspace from a culture suspected of comprising *Aspergillus* isolated from a subject; detecting the presence in the sample of one, two, three, or more volatile organic compounds (VOCs) produced by the *Aspergillus* species in a sample comprising breath from the subject or headspace from a culture suspected of comprising *Aspergillus* isolated from the subject, wherein the VOCs are selected from the group consisting of farnesene, beta-vatirenene, cis-geranylacetone, camphene, alpha-pinene, beta-pinene, limonene, alpha-bergamotene, farnesene, elixene, alpha-santalene, beta-elemene, acoradien, chamigrene, 1,5,9-trimethyl cyclododecatriene, 9-decene-2-one and beta-sesquiphellandrene; and diagnosing a subject as having IA based on the presence of (i.e., when there are) one, two, three or more of the VOCs in the sample.

In some embodiments, the methods include detecting the presence in the sample of one, two or three VOCs selected from the group consisting of farnesene, beta-vatirenene and cis-geranylacetone; and diagnosing a subject who has one, two or all three of farnesene, beta-vatirenene and cis-geranylacetone in the sample as having IA. In preferred embodiments, a diagnosis of IA is based on the presence of all three of the VOCs farnesene, beta-vatirenene and cis-geranylacetone in the sample.

In another aspect, the invention provides methods for treating a subject who has invasive aspergillosis (IA). The methods include obtaining a sample comprising breath of a subject or headspace from a culture suspected of comprising *Aspergillus* isolated from a subject; detecting the presence in the sample of one, two or three VOCs selected from the group consisting of farnesene, beta-vatirenene and cis-geranylacetone, and administering an antifungal treatment to a subject who has one, two or all three of farnesene, beta-vatirenene and cis-geranylacetone in their breath.

In some embodiments, the treatment includes administration of one or more doses of one or more antifungal compounds, e.g., an amphotericin B formulation; an azole compound; and an echinocandin.

In another aspect, the invention provides methods for detecting the presence of an *Aspergillus fumigatus, A. terreus*, or *A. calidoustus* infection in a subject. The methods include obtaining a sample comprising breath of a subject, or headspace from a culture suspected of comprising *Aspergillus* isolated from a subject; determining the presence of one, two, three, or more, e.g., all, of the VOCs selected from the group consisting of camphene, alpha-pinene, beta-pinene, limonene, alpha-bergamotene, farnesene, elixene, alpha-santalene, beta-elemene, acoradien, chamigrene, 1,5,9-trimethyl cyclododecatriene, 9-decene-2-one and beta-sesquiphellandrene in the sample. The presence of one, two, three, or more, e.g., all, of camphene, alpha-pinene, beta-pinene, limonene, alpha-bergamotene, or farnesene indicates the presence of an *A. fumigatus* infection; the presence of one, two, three, or more, e.g., all, of elixene, alpha-santalene, beta-elemene, acoradien, chamigrene, and 1,5,9-trimethyl cyclododecatriene indicates the presence of an *A. terreus* infection; and the presence of one or both of 9-decene-2-one and beta-sesquiphellandrene indicates the presence of an *A. calidoustus* infection in the subject.

In some embodiments, the methods include selecting, and optionally administering, a therapy comprising an azole, e.g., voriconazole, for a subject who has an *A. fumigatus* or *A. terreus* infection; or selecting, and optionally administering, a therapy comprising amphotericin B (AMB), e.g., D-AMB or a lipid formulation of AMB, for a subject who has an *A. calidoustus* infection.

In another aspect, the invention provides methods for monitoring efficacy of a treatment for invasive aspergillosis (IA) in a subject. The methods include determining a first level of one, two, three, or more volatile organic compounds (VOCs) produced by the *Aspergillus* species in a sample comprising breath from the subject or headspace from a culture suspected of comprising *Aspergillus* isolated from the subject, wherein the VOCs are selected from the group consisting of farnesene, beta-vatirenene, cis-geranylacetone, camphene, alpha-pinene, beta-pinene, limonene, alpha-bergamotene, farnesene, elixene, alpha-santalene, beta-elemene, acoradien, chamigrene, 1,5,9-trimethyl cyclododecatriene, 9-decene-2-one and beta-sesquiphellandrene, in the subject; administering a treatment for IA to the subject; determining a second level of the VOCs in a sample obtained after administration of the treatment to the subject; and comparing the first and second levels of VOCs. A decrease in the VOCs indicates that the treatment has been effective in treating the IA in the subject, and an increase or no change indicates that the treatment has not been effective in treating the IA in the subject.

In some embodiments, the treatment includes administration of one or more doses of one or more antifungal compounds, e.g., an amphotericin B formulation; an azole compound; and an echinocandin.

In yet another aspect, the invention provides methods for identifying a candidate compound for the treatment of IA. The methods include providing a test culture comprising one or more *Aspergillus* species; detecting a baseline level of fungal VOCs in the headspace of the culture in the absence of the test compound, wherein the VOCs are selected from the group consisting of farnesene, beta-vatirenene, cis-geranylacetone, camphene, alpha-pinene, beta-pinene, limonene, alpha-bergamotene, farnesene, elixene, alpha-santalene, beta-elemene, acoradien, chamigrene, 1,5,9-trimethyl cyclododecatriene, 9-decene-2-one and beta-sesquiphellandrene, in the subject; contacting the test culture with a test compound; determining a second level of the VOCs in a the test culture; comparing the second level of VOCs to the baseline level; and identifying a test compound that decreases levels of fungal VOCs in the test culture as a candidate compound for the treatment of IA.

In another aspect, the invention provides methods for detecting the presence of an *Aspergillus fumigatus*, *A. terreus*, or *A. calidoustus* infection in a culture. The methods include obtaining a sample from the culture, e.g., gas from the headspace of the culture; determining the presence of one, two, three, or more, e.g., all, of the VOCs selected from the group consisting of camphene, alpha-pinene, beta-pinene, limonene, alpha-bergamotene, farnesene, elixene, alpha-santalene, beta-elemene, acoradien, chamigrene, 1,5,9-trimethyl cyclododecatriene, 9-decene-2-one and beta-sesquiphellandrene in the sample. The presence of one, two, three, or more, e.g., all, of camphene, alpha-pinene, beta-pinene, limonene, alpha-bergamotene, or farnesene indicates the presence of *A. fumigatus* in the culture; the presence of one, two, three, or more, e.g., all, of elixene, alpha-santalene, beta-elemene, acoradien, chamigrene, and 1,5,9-trimethyl cyclododecatriene indicates the presence of *A. terreus* in the culture; and the presence of one or both of 9-decene-2-one and beta-sesquiphellandrene indicates the presence of *A. calidoustus* infection in the culture.

In some embodiments of the various methods described herein, determining the presence of a VOC comprises assaying the sample to detect the presence the VOC. In some embodiments, assaying the sample to detect the presence the VOC comprises using a gas chromatography (GC) or spectrometry method. In some embodiments, the spectrophotometry method is mobility spectrometry (IMS) or differential mobility spectrometry (DMS).

In some embodiments of the various methods described herein, the subject is a human.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 9. Modulation of key *A. fumigatus* VOCs with antifungal therapy. A) GC-MS TIC of *A. fumigatus* with the addition of micafungin, showing initial increase in key VOCs at 24 hours. B) GC-MS TIC of *A. fumigatus* with the addition of voriconazole, showing near-complete attenuation in key VOCs at 24 hours.

DETAILED DESCRIPTION

Figure 1:
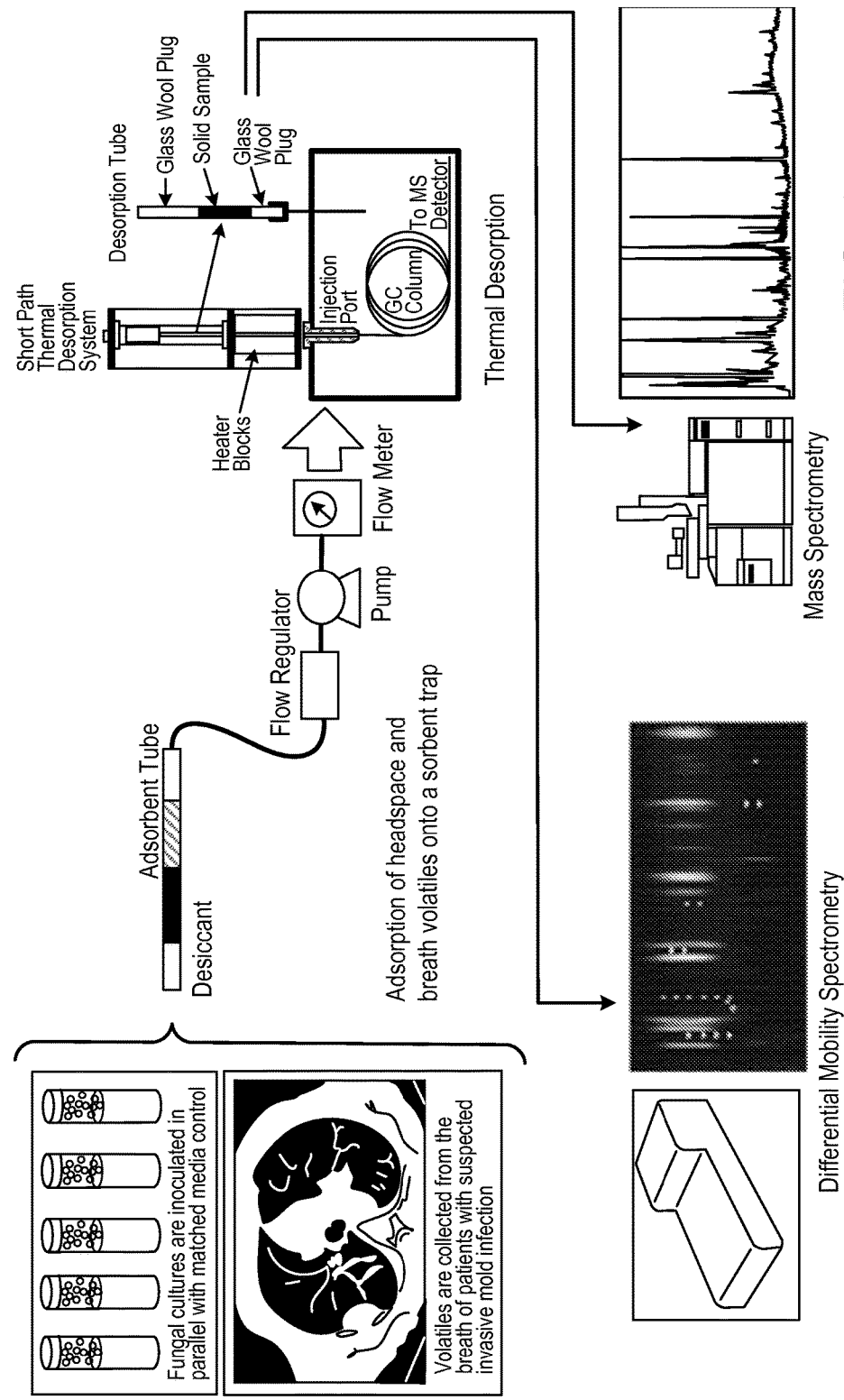
FIG. 1. Collection of VOCs from headspace gas of in vitro cultures or patient breath, with concentration of VOCs on a thermal desorption trap, thermal desorption onto the GC, and parallel data acquisition on a dual mass spectrometry/differential mobility spectrometry system.

Pathogenic molds produce VOCs as part of their normal metabolism. Agricultural and environmental health industries have previously investigated the detection of microbial VOCs to identify spoiled grain and mold-infested 'sick buildings,' respectively, and investigators in these areas have noticed species-specific differences in the composition of VOCs emitted by molds in these settings.

As described herein, the present inventors have identified unique, species-specific VOC profiles of *A. fumigatus, A. terreus*, and *A. calidoustus* in vitro, including several volatile terpene and sesquiterpene compounds that can be used to discriminate these species from each other and from other molds, and demonstrated that differential mobility spectrometry (DMS) can be used for the rapid discrimination of fungal species using pattern-based identification of these species-specific VOC profiles. The key terpene and sesquiterpene compounds identified in in vitro cultures of *A. fumigatus* were also present in the breath of patients with IA, in addition to novel *Aspergillus* VOCs induced in vivo, namely, the sesquiterpene beta-vatirenene and the oxidized farnesene derivative cis-geranylacetone. A combination of farnesene, beta-vatirenene, and cis-geranylacetone accurately distinguished patients with IA from patients with other causes of pneumonia with 93% sensitivity and 96% specificity.

Detection of these unique VOC profiles can be harnessed for species-level identification of *Aspergillus* and other mold species in the laboratory, and direct detection of these fungal volatile profiles in the breath of patients with suspected IA can be used for the rapid, noninvasive, highly accurate, and species-specific diagnosis of IA and other fungal pneumonias. The methods and devices described herein, e.g., the DMS-based detection methods, can be adapted to a small, portable bedside breath gas detection system for real-time patient breath surveillance for this pattern of fungal metabolites, to allow for earlier IA diagnosis than currently possible, more rational test-based prescribing of antifungal medications, monitoring of clinical response to antifungal therapy, and ultimately, better patient outcomes.

As described herein, among other uses, these VOC profiles can be used for:

a. rapid, noninvasive, sensitive, and species-specific breath tests for the diagnosis of invasive aspergillosis and the discrimination of aspergillosis from other causes of pneumonia in the growing population of immunocompromised patients at risk for invasive fungal infections;

b. surrogate marker demonstrating successful antifungal treatment of IA, and c. rapid identification and antifungal susceptibility testing of *Aspergillus* species, e.g., in the microbiology laboratory, based on their VOC profile (i.e., the VOCs present in the sample).

Invasive Aspergillosis

The methods described herein can be used to detect or diagnose invasive aspergillosis (IA) in a subject, to select treatment and to treat IA, and to monitor treatment of IA. The methods can be used in the different forms of invasive aspergillosis, including invasive pulmonary aspergillosis, sinus or nasal aspergillosis, disseminated aspergillosis, and single-organ invasive aspergillosis, e.g., of an organ in the sino/nasal/respiratory tract (see, e.g., Walsh et al., Clinical Infectious Diseases 2008; 46:327-60; Milroy et al., J Clin Pathol. 1989 February; 42(2): 123-127). In preferred embodiments, the methods described herein can be used for subjects with invasive pulmonary aspergillosis.

Samples

The methods described herein can be performed on a gas or liquid sample. In some embodiments, the sample is exhaled breath directly from an individual or from a breathing machine such as a ventilator. Alternatively, the methods can be performed using headspace from a culture known or suspected to include *Aspergillus* species, e.g., commercially-available or lab-cultured species or species obtained from a primary sample from a subject, e.g., a clinical sample obtained by biopsy of the affected area (e.g., nasal biopsy, transthoracic percutaneous needle aspiration, or video assisted thoracoscopic biopsy) or bronchoalveolar lavage. The sample is maintained in a suitable growth medium to allow growth and metabolism of any *Aspergillus* species in the sample. In certain embodiments, the invention involves taking a clinical sample from a subject and placing it in media, for example, with microfluidics, or in culture, for example, with conventional culturing methods. The *Aspergillus* species, if present, are stimulated to metabolize. The headspace (gaseous phase) generated as a result of this metabolism can be collected and analyzed using a method described herein or known in the art, see, e.g., US20100291617. In some embodiments, the methods are performed directly on bronchoalveolar washings, obtained by bronchoscopy/bronchoalveolar lavage. In some embodiments, the sample is a gas, e.g., patient breath or gas from the headspace of an in vitro culture sample. Where headspace gas is used, the gas should be collected after the headspace has been in contact with the culture for a sufficient amount of time for the compounds to be present, preferably in an air-tight, sealed environment.

The VOCs can also be detected in a liquid sample, since they are expected to be there in equilibrium with the gaseous phase. Thus, in addition to or as an alternative, the samples assayed using the methods described herein can include a liquid, e.g., blood (e.g., plasma or serum), lymph, urine, tears, saliva, sputum, nasal mucus, phlegm (e.g., expectorate), or CSF from a subject (e.g., from a biological fluid that comes near or preferably into contact with the tissue or organ that is known or suspected to be infected with an *Aspergillus* species), or the liquid phase (e.g., supernatant) of an in vitro culture. In some embodiments, the sample comprises saliva from the subject.

Detection Methods

A number of methods known in the art can be used to detect the presence of the VOCs described herein in a sample. Exemplary methods (particularly for use with a gas sample) include gas chromatography (GC); spectrometry, for example mass spectrometry (including quadrapole, time of flight, tandem mass spectrometry, ion cyclotron resonance, and/or sector (magnetic and/or electrostatic)), ion mobility spectrometry, field asymmetric ion mobility spectrometry, and/or DMS; fuel cell electrodes; light absorption spectroscopy; nanoparticle technology; flexural plate wave (FPW) sensors; electrochemical sensors; photoacoustic equipment; laser-based equipment; electronic noses (bio-derived, surface coated); and various ionization techniques. See, e.g., US20100291617 and US20070003996. Preferred methods include ion mobility spectrometry (IMS) or differential mobility spectrometry (DMS).

In some embodiments, the methods described herein include the use of differential mobility spectrometry to detect VOCs in a sample. An exemplary micro-machined differential mobility spectrometer (DMS), developed for chemical and biological sensing applications, is currently available from Sionex Corporation. DMS has several features that make it an excellent platform for VOC analysis: it is quantitative, selective, and exquisitely sensitive, with a volatile detection limit in the parts-per-trillion range (Davis et al., In: 12th International Conference on Transducers, Solid-State Sensors, Actuators and Microsystems; 2003; p. 1233-8 vol. 2; Miller et al., In: Solid-State Sensors and Actuators Workshop; 2000; Hilton Head, S.C.; 2000; Krebs et al., Sensors Journal, IEEE 2005; 5(4):696-703). Unlike mass spectrometry, which separates particles based on mass/charge ratios, DMS harnesses differences in ion mobility in low and high electric fields to achieve a gas-phase separation of ions at atmospheric pressure. DMS rapidly detects compounds that are difficult to resolve by other analytical techniques such as mass spectrometry in challenging matrices such as human breath (Kanu et al., J Mass Spectrom 2008; 43:1-22; Kanu et al., J Chromatogr A 2008; 1177:12-27; Luong J et al., J Chromatogr Sci 2006; 44:276-286; Nazarov et al., Anal Chem 2006; 7697-706; Kolakowski et al., Analyst 2007; 132:842-64).

DMS can be tuned to monitor specific ion masses, thus tailoring response characteristics to focus on various compounds of interest. It requires no reagents, generates the high fields required by the sensor using a small power supply, and has already been microfabricated, resulting in a small, portable machine that can be used at the bedside, with a turnaround time of several minutes. DMS has been used successfully in several commercial settings, including a hand-held, portable detector of trace levels of chemical warfare agents from General Dynamics (JUNO™) and airport explosives detectors from Thermo (see, e.g., U.S. Pat. No. 7,605,367). DMS technology has also been successfully applied to the characterization of unique VOCs produced by *Mycobacterium tuberculosis* and other bacteria (Fong et al., Anal Chem 2011; 83:1537-46; Shnayderman et al., Anal Chem 2005; 77:5930-7).

To perform a measurement using a DMS, a gas sample is introduced into the spectrometer, where it is ionized, and the ions are transported through an ion filter towards the detecting electrodes (Faraday plates) by a carrier gas. The DMS device can separate chemical components of a substance based on differing ion mobilities. For other devices, measurements are performed using methods known in the art.

Additional non-limiting examples of systems that can be used in the present methods include those described in US20090078865; US20130168548; US20100291617 and US20070003996.

In some embodiments, the methods include obtaining a sample of ambient air and detecting the presence and/or levels of VOCs in the air, to provide a reference for subtraction of ambient VOCs.

A number of methods are known in the art for detecting the presence and/or levels of the VOCs in a liquid sample, including but not limited to chromatography (e.g., HPLC) and spectrophotometry (e.g., MS, LC-MS, MALDI-TOF, and other of the methods described above for gas-phase samples).

Combination Diagnostics

In some embodiments, the methods include performing an additional diagnostic test for IA. A number of such tests are known in the art and include galactomannan enzyme immunoassays; radiology imaging studies (e.g., CT imaging); bronchoalveolar lavage, transthoracic percutaneous needle aspiration, or video assisted thoracoscopic biopsy. A positive result on one of these tests can provide further evidence supporting a diagnosis of IA; see, e.g., Walsh et al., Clinical Infectious Diseases 2008; 46:327-60.

*Aspergillus* Species Identification and Diagnosis

As described herein, *A. fumigatus, A. terreus, A. calidoustus* each produce VOCs that can be used to identify them in a sample, e.g., in a sample comprising breath of a subject, or headspace from a culture suspected of comprising *Aspergillus*; the culture can be, e.g., a culture of a biopsy from a subject, or a culture in a microbiology laboratory, e.g., a culture known or suspected of containing or being contaminated with an *Aspergillus* species. This identification can be used to diagnose a subject with the specific species of *Aspergillus*, allowing for the administration of species-specific treatments, e.g., as described below.

Thus, the methods described herein can include obtaining a sample comprising breath of a subject, or headspace from a culture suspected of comprising *Aspergillus*, and detecting and identifying the VOCs in the sample. For example, the methods can include detecting the presence of one, two, three, or more, e.g., all, of camphene, alpha-pinene, beta-pinene, limonene, alpha-bergamotene, farnesene, elixene, alpha-santalene, beta-elemene, acoradien, chamigrene, 1,5,9-trimethyl cyclododecatriene, 9-decene-2-one and beta-sesquiphellandrene in the sample. The presence of one, two, three, or more, e.g., all, of camphene, alpha-pinene, beta-pinene, limonene, alpha-bergamotene, or farnesene indicates the presence of *A. fumigatus* in the sample (and thus an *A. fumigatus* infection in cases where the sample is from a subject); the presence of one, two, three, or more, e.g., all, of elixene, alpha-santalene, beta-elemene, acoradien, chamigrene, and 1,5,9-trimethyl cyclododecatriene indicates the presence of *A. terreus* in the sample (and thus an *A. terreus* infection in cases where the sample is from a subject); and the presence of one or both of 9-decene-2-one and beta-sesquiphellandrene indicates the presence of *A. calidoustus* in the sample (and thus an *A. calidoustus* infection in cases where the sample is from a subject). In some embodiments, where limonene or alpha-pinene is present, at least one or two other VOCs must also be present for a positive species identification, and a species-specific diagnosis, to be made.

Methods of Treatment

The methods described herein can be used to select a treatment for a subject, and can optionally include administering the treatment to a subject. When a subject has been diagnosed by a method described herein as having IA, then a treatment comprising administration of a therapeutically effective amount of an antifungal compound can be administered.

A number of antifungal compounds are known in the art and under development. At present, deoxycholate amphotericin B (D-AMB) and its lipid formulations (AMB lipid complex (ABLC), liposomal amphotericin B (LAMB), and Amphotericin B cholesteryl sulfate complex (AMB colloidal dispersion, ABCD)); azole compounds (itraconazole, voriconazole, posaconazole); and echinocandins (caspofungin, micafungin, anidulafungin) are in clinical use, though voriconazole and D-AMB are the only compounds approved for primary treatment of invasive aspergillosis in the United States. For detailed information on treatment of IA, see, e.g., Walsh et al., Clinical Infectious Diseases 2008; 46:327-60; and Marr et al., *Treatment and prevention of invasive aspergillosis*, Up-To-Date (topic updated on Oct. 18, 2012; literature review August 2013; available at uptodate.com/contents/treatment-and-prevention-of-invasive-aspergillosis?topicKey=ID %2F2459&elapsedTimeMs= 7&view=print&displayedView=full).

In some embodiments, the methods include selecting and optionally administering an azole antifungal, e.g., itraconazole (ITR), voriconazole (VOR), posaconazole (POS), ravuconazole (RAV), or isavuconazole (ISA), or an amphotericin B (AMB) formulation as described above, to a subject identified by a method described herein as having IA. In some embodiments, the methods include administering an echinocandin, e.g., caspofungin, micafungin or anidulafungin, e.g., alone or in combination with an azole (e.g., voriconazole) or AMB.

It is known that triazoles are not active against some isolates of *A. calidoustus,* and some *A. terreus* isolates are resistant to AMB. See, e.g., Baddley et al., J. Clin. Microbiol. 2009, 47(10):3271. Thus, in some embodiments, where the species of *Aspergillus* is determined, an azole compound (e.g., ITR, VOR, POS, RAV, or ISA) is selected for (and optionally administered to) a subject who has *A. fumigatus* or *A. terreus*, but not *A. calidoustus*. In some embodiments, an AMB (e.g., D-AMB, ABLC, LAMB, or ABCD) is selected for (and optionally administered to) a subject who has *A. calidoustus*. In some embodiments, an AMB is selected for (and optionally administered to) a subject who has *A. fumigatus*, but not a subject who has *A. terreus*.

In some embodiments, the methods described herein can be used to determine susceptibility of *Aspergillus* species, e.g., to treatment with a known or suspected antifungal, e.g., in the microbiology laboratory. A sample suspected or known to include *Aspergillus* from a subject is obtained and cultured as described above, e.g., under conditions mimicking the in vivo environment, and then exposed to a potential treatment (e.g., a known or experimental treatment). After exposure to the treatment, the VOCs present in the headspace of the culture are sampled. If the treatment decreases VOCs as compared to a reference level (e.g., a level of VOCs in the headspace before exposure to the treatment), then the *Aspergillus* in the sample is considered susceptible to the treatment. In this case, the treatment is likely to be effective in treating IA in the subject; the treatment can be selected and optionally administered to subject.

Monitoring Treatment Efficacy

As described herein, successful treatment of an *Aspergillus* infection results in a decrease in fungal VOCs. Thus, the methods can include repeated assays of VOC levels in a subject, e.g., before, during, and after administration of a treatment for IA. A decrease in VOC levels would indicate that the treatment has been successful. In some embodiments, levels of one, two, or all three of farnesene, beta-vatirenene, and/or cis-geranylacetone are determined. In some embodiments, levels of one, two, three, or more of farnesene, beta-vatirenene, cis-geranylacetone, camphene, alpha-pinene, beta-pinene, limonene, alpha-bergamotene, farnesene, elixene, alpha-santalene, beta-elemene, acoradien, chamigrene, 1,5,9-trimethyl cyclododecatriene, 9-decene-2-one and beta-sesquiphellandrene are determined.

Methods of Identifying Novel Antifungal Agents

Included herein are methods for screening test compounds, e.g., polypeptides, polynucleotides, inorganic or organic large or small molecule test compounds, to identify agents useful in the treatment of IA.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample comprising one or more *Aspergillus* species, and the ability of the test compound to decrease levels of a VOC as described herein in the headspace of the culture is determined.

In some embodiments, the test sample is, or is derived from (e.g., a sample taken from) an in vivo model of a disorder as described herein. For example, an animal model, e.g., a rodent (such as a rat or mouse) that has been infected with one or more *Aspergillus* species can be used.

A test compound that has been screened by a method described herein and determined to decrease VOCs, can be considered a candidate compound. A candidate compound that has been screened, e.g., in an in vivo model of a disorder, e.g., a rodent infected with one or more *Aspergillus* species, and determined to decrease VOCs in a sample comprising breath from the infected animal model or headspace from a culture of a sample from the infected animal model, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" (e.g., test compounds that decrease fungal VOCs in an animal model) in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating IA. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to an animal model of IA, as described herein. The animal can be monitored for a change in the disorder, e.g., for an improvement in a parameter of the disorder, e.g., a parameter related to clinical outcome. In some embodiments, the parameter is VOCs or survival, and an improvement would be a reduction in VOCs or an increase in survival. In some embodiments, the subject is a human, e.g., a human with IA and the parameter is levels of fungal VOCs or survival.

EXAMPLES

The invention is further described in the following examples, which do not limit the scope of the invention described in the claims.

Example 1. Definition of *Aspergillus* VOC Profiles In Vitro

Using gas chromatography interfaced to mass spectrometry and differential mobility spectrometry (GC-MS/DMS), VOC profiles were characterized in the headspace gas of in vitro cultures of *Aspergillus* species pathogenic to humans, most notably *A. fumigatus*. *A. terreus*, and *A. calidoustus*, under incubation conditions designed to mimic the milieu of the human lung and promote hyphal growth (as *Aspergillus* spreads through hyphal growth and invasion of human tissue blood vessels and tissues in vivo).

Mold strains (Table 1) were incubated at 25° C. on Sabouraud dextrose agar slants. Conidia were harvested and conidial suspensions were prepared in sterile water. Conidia were quantified with a hemocytometer.

TABLE 1

Fungal species used for in vitro VOC profile determination

| Genus | Species | Strains (N) | Source* |
|---|---|---|---|
| Aspergillus | fumigatus | 9 | ATCC, CDC, BWH |
| Aspergillus | terreus | 7 | ATCC, BWH |
| Aspergillus | calidoustus | 3 | ATCC |
| Aspergillus | niger | 6 | CDC, BWH |
| Aspergillus | tubingensis | 2 | CDC |
| Aspergillus | flavus | 5 | CDC, BWH |
| Rhizopus | oryzae | 3 | ATCC, BWH |
| Fusarium | solani | 2 | ATCC, BWH |
| Mucor | velutinosus | 1 | BWH |

*ATCC: American Type Culture Collection, CDC: Centers for Disease Control; BWH: Brigham and Women's Hospital For each experiment, $10^4$ conidia were inoculated into 5 mL of microbial media (either nutrient Yeast Extract Peptone Dextrose (YPD) broth, nutrient poor *Aspergillus* minimal media (Pontecorvo et al., Advan Genet 1953; 5:141-238), or under iron-starved, alkaline stress, or nitrogen-depleted conditions (McDonagh et al., PLoS Pathog 2008; 4:e1000154)) in 20 mL glass vials with an airtight crimp top incorporating a rubber septum. Cultures were incubated for 24-144 hours at 200 rpm and 37° C. and headspace gas was dynamically adsorbed, using argon carrier gas and an air sampling pump calibrated to 20 mL/minute, onto Markes thermal desorption traps containing tandem beds of Tenax TA (200 mg), Carbograph 1 TD (100 mg), and Carboxen 1003 (100 mg), optimized to retain VOCs of diverse size and polarity.

Headspace VOCs were also collected after exposure of a subset of fungal isolates to the antifungal drugs voriconazole, liposomal amphotericin B, and micafungin, each at a concentration of 1.0 mg/mL.

VOCs were desorbed onto a dual GC-MS/DMS system (FIG. 1)—the eluent from the gas chromatograph was split between the MS, to allow identification of each compound, and the DMS, an extremely sensitive and selective gas detector that can be easily used as a point-of-care gas detection device, to determine the mobility pattern for each compound. The NIST MS Search 2.0 Library was used to identify VOCs in the total ion chromatogram (TIC) of the GC-MS data. Differences in spectral features of DMS output were visually distinguished between the positive ion spectra of *A. fumigatus* and *A. terreus* and principal component analysis (PCA) was used to evaluate the degree of class discrimination between these fungal species using algorithms in MATLAB (Version R2012a).

Collection of VOCs in Patient Breath

Breath was collected from patients with suspected IA using a Loccioni Breath Analysis sampler. For each patient, up to 4 minutes of tidal breath was adsorbed using an air sampling pump calibrated to 900 mL/minute onto two parallel thermal desorption traps containing tandem beds of Tenax TA (200 mg), Carbograph 1 TD (100 mg), and Carboxen 1003 (100 mg). Ambient air was sampled concurrently with each breath sample at a flow rate of 900 mL per minute to control for any environmental VOCs in patient breath samples. These samples were analyzed using the same thermal desorption GC-MS method outlined above for the in vitro fungal cultures.

Results

Figure 2A:
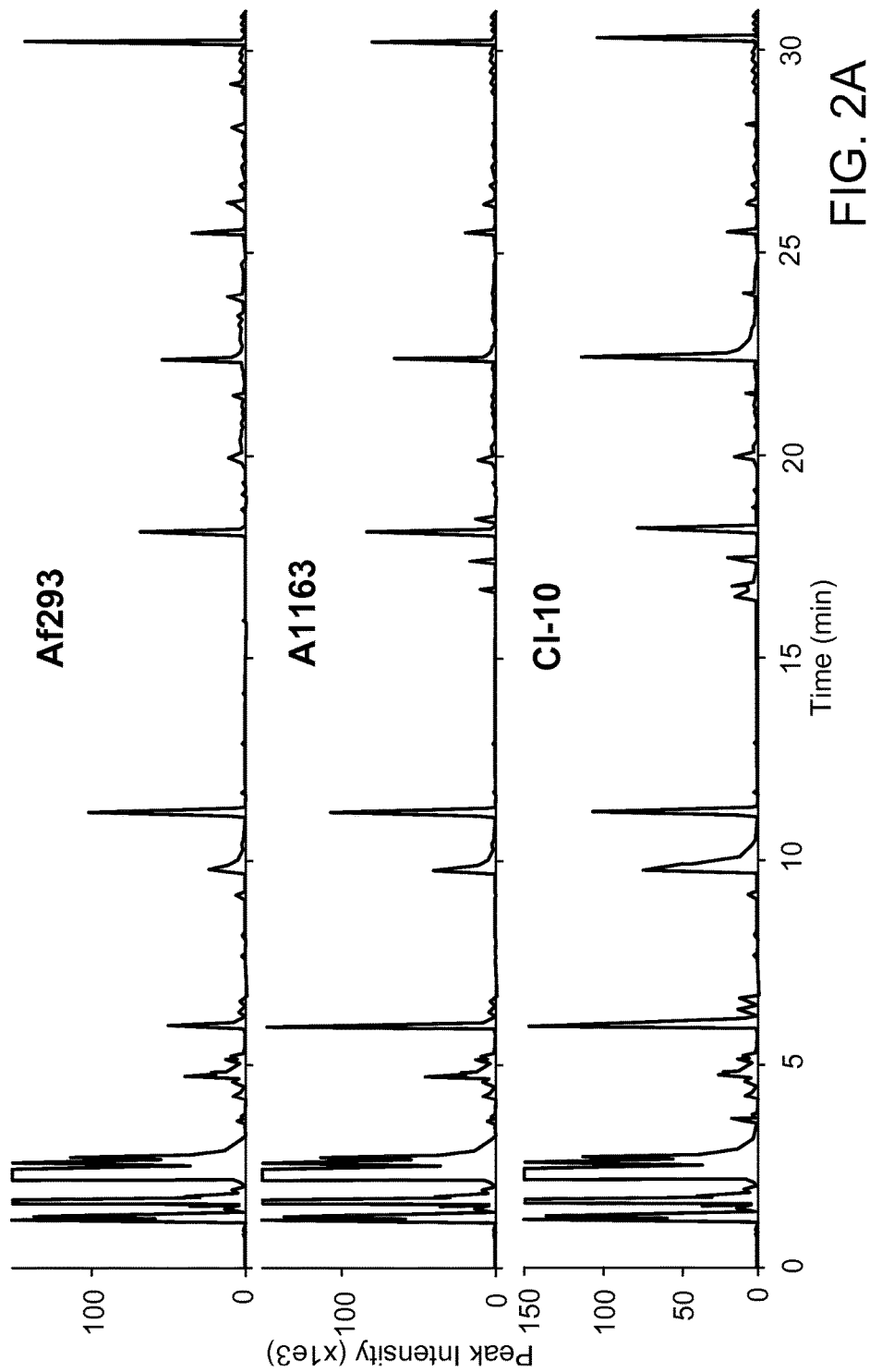
FIG. 2. A) Total ion chromatograms (TIC) generated by GC-MS of reference and clinical strains of *A. fumigatus* at 96 hrs in YPD media, showing the reproducibility of the VOC profile within species. B) GC-MS TIC of common pathogenic fungal species, showing interspecies VOC profile heterogeneity.
Figure 2B:
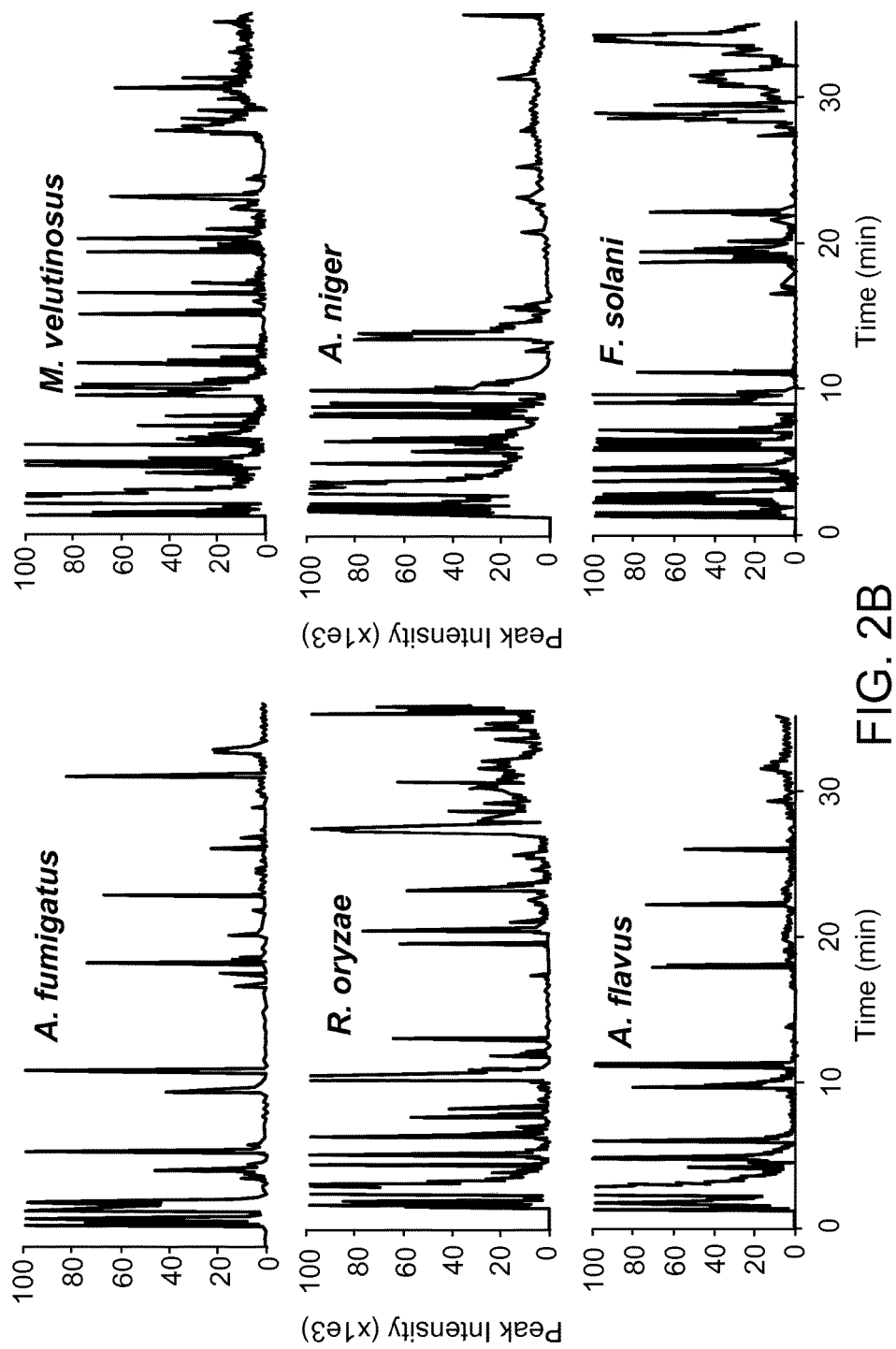

Intraspecies Homogeneity. Interspecies Heterogeneity of VOC Profiles:

Each mold species tested in vitro produced a distinctive VOC profile that was conserved within each species (FIG. 2A) and distinct between species (FIG. 2B). Terpene and sesquiterpene compounds were particularly distinct between different fungal species.

Figure 3:
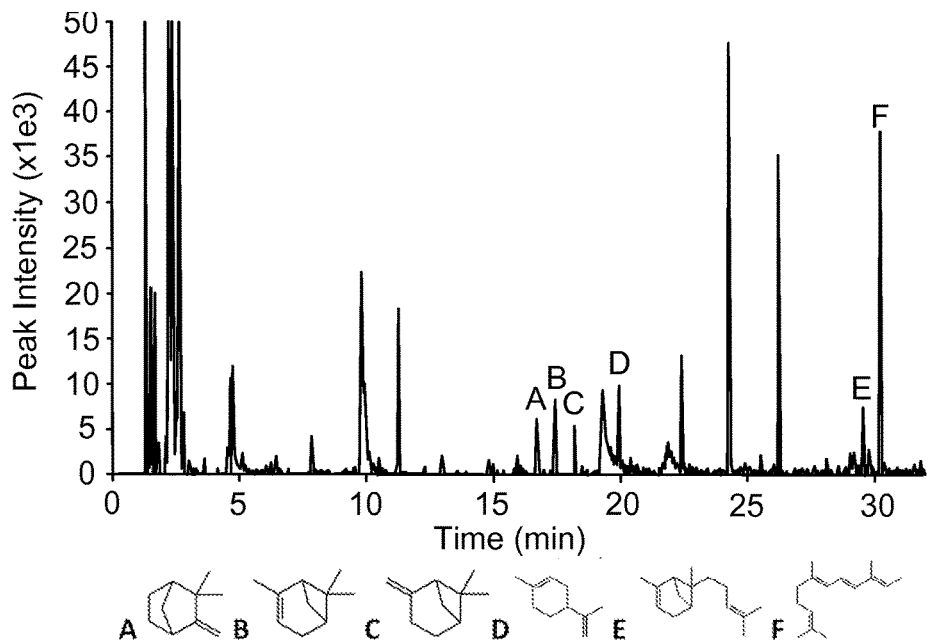
FIG. 3. Key features of the *A. fumigatus* VOC profile: A. camphene, B. α-pinene, C. β-pinene, D. limonene, E. α-bergamotene, and F. farnesene.
Figure 4:
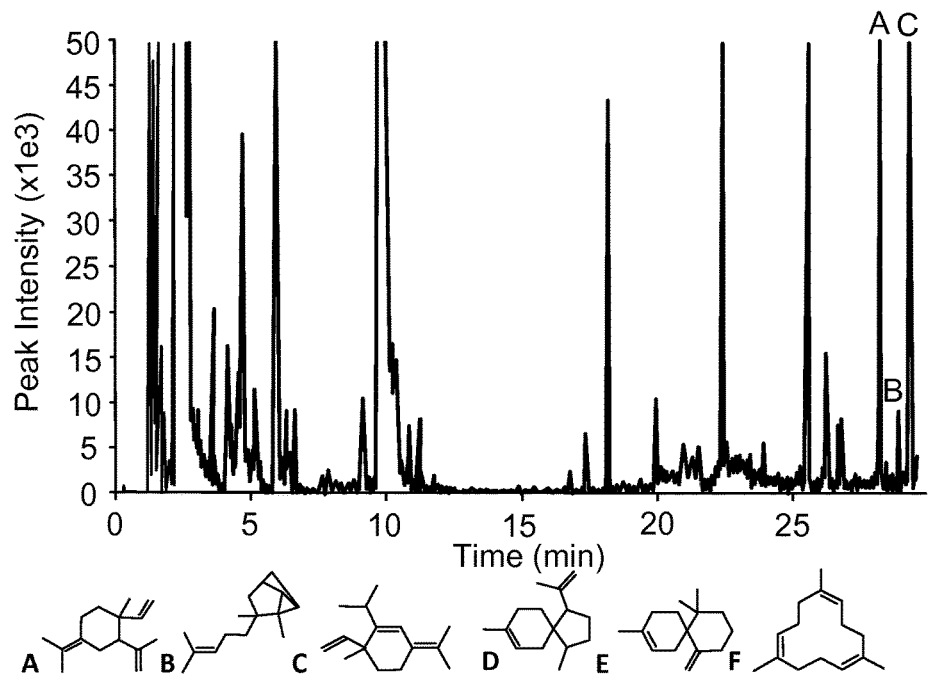
FIG. 4. Key features of the *A. terreus* VOC profile: A. elixene, B. α-santalene, C. β-elemene, D. acoradien, E. chamigrene, and F. 1,5,9-trimethyl cyclododecatriene.
Figure 5:
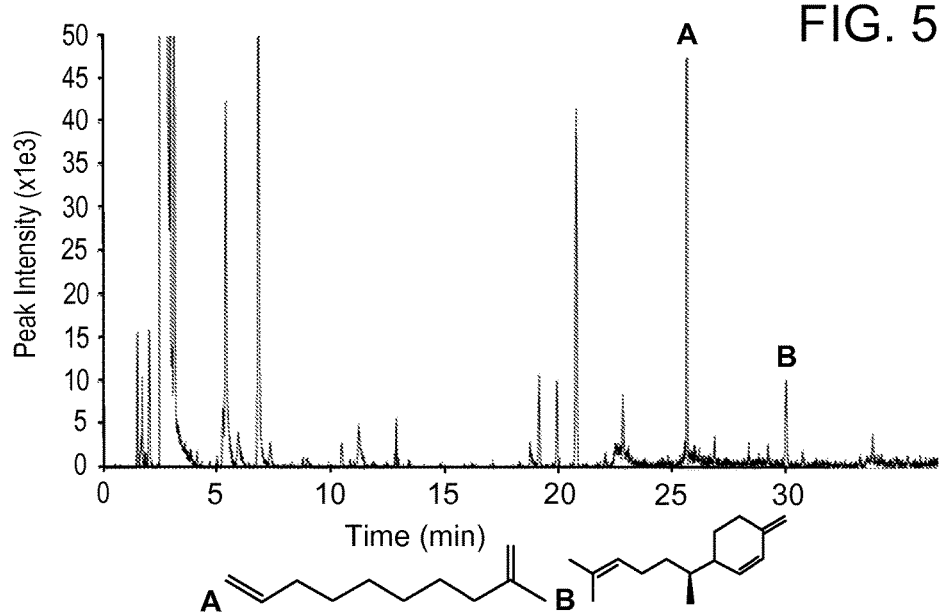
FIG. 5. Key features of the *A. calidoustus* VOC profile: A. 9-decene-2-one, B. β-sesquiphellandrene.

Comparison of the VOC profile of *A. fumigatus* with other fungal species showed that camphene, alpha-pinene, beta-pinene, limonene, alpha-bergamotene, and farnesene were characteristic of *A. fumigatus* (FIG. 3). Comparison of the VOC profile of *A. terreus* with other fungal species showed that elixene, alpha-santalene, beta-elemene, acoradien, chamigrene, and 1,5,9-trimethyl cyclododecatriene were key features characteristic of *A. terreus* (FIG. 4). Comparison of the VOC profile of *A. calidoustus* with other fungal species showed that 9-decene-2-one and beta-sesquiphellandrene were key VOC features characteristic of *A. calidoustus* (FIG. 5).

Figure 6:
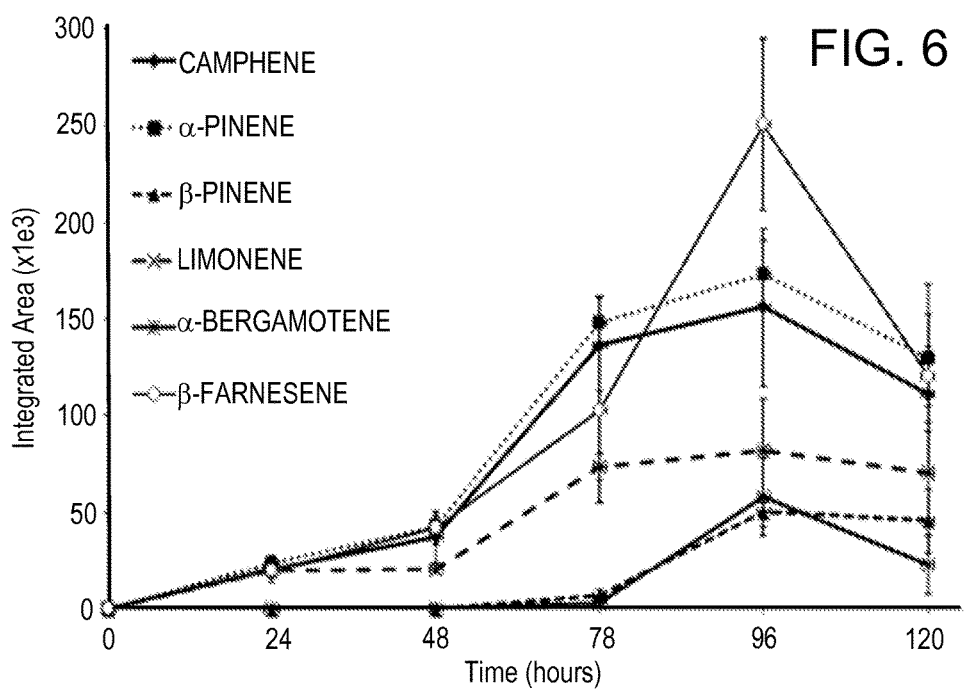
FIG. 6. Kinetics of *A. fumigatus* VOC emission with hyphal growth.

Kinetics of VOC Production In Vitro:

The kinetics of VOC release were assessed in vitro over lag, log, stationary, and death phases of each mold species, over 24-144 hours of incubation at 37° C. The key VOC features of *A. fumigatus* were first clearly discernible at 24 hours of incubation and all volatiles reached their peak concentration at 96 hours of incubation (FIG. 6).

Figure 7:
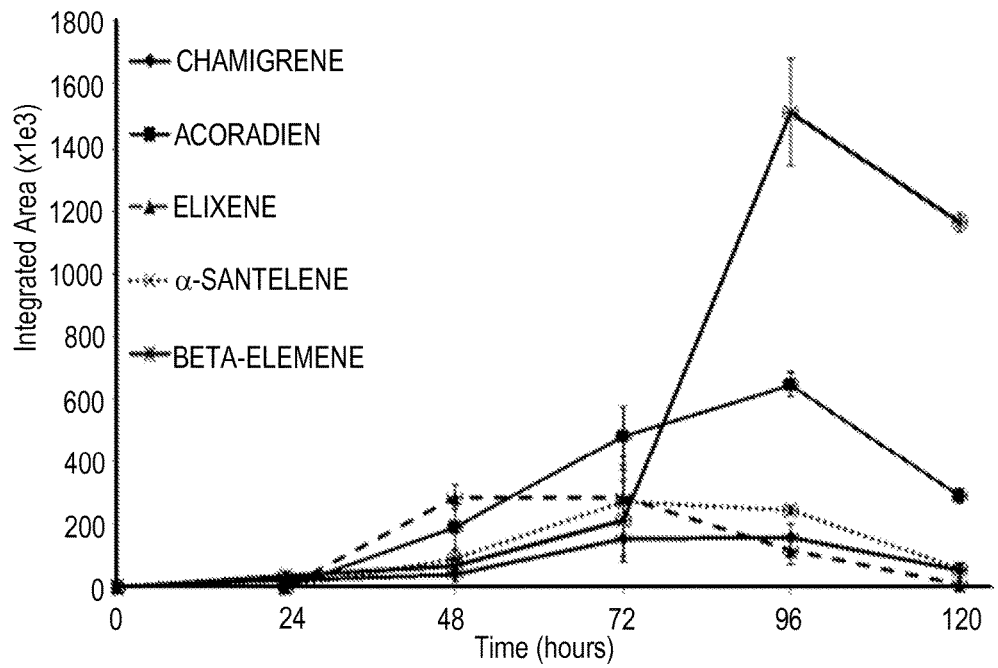
FIG. 7. Kinetics of *A. terreus* VOC emission with hyphal growth.

The key VOC features of *A. terreus* were first clearly discernible at 48 hours of incubation and reached peak levels at 96-120 hours of incubation (FIG. 7).

Figure 8:
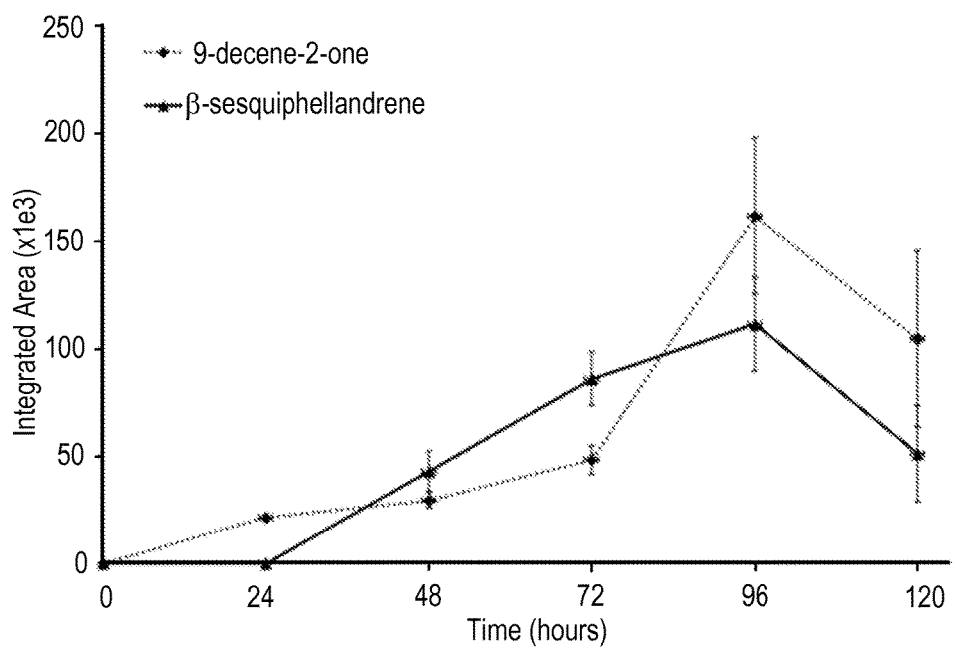
FIG. 8. Kinetics of *A. calidoustus* VOC emission with hyphal growth.

The key VOC features of *A. calidoustus* were first clearly discernible at 24-48 hours of incubation and reached their peak at 96 hours of incubation (FIG. 8).

Antifungal Exposure Modulates the Release of VOCs in *A. fumigatus*:

Whether exposure to antifungal drugs might modulate VOC release in *Aspergillus fumigatus* was assessed in vitro. When micafungin was added to 48-hour hyphal cultures of *A. fumigatus*, up to a 17-fold increase in some of the key *A. fumigatus* VOC features was observed after 24 hours, compared to matched control samples without micafungin (FIG. 9A); attenuation of these VOC features was observed with a longer duration of incubation and hyphal death. A similar initial increase then attenuation in key *A. fumigatus* VOCs was observed in response to liposomal amphotericin B. When voriconazole was added to 48-hour hyphal cultures of *A. fumigatus*, near-complete attenuation of the key VOC features of this species was observed after 24 hours, compared to matched control samples without voriconazole (FIG. 9B).

Figure 10A:
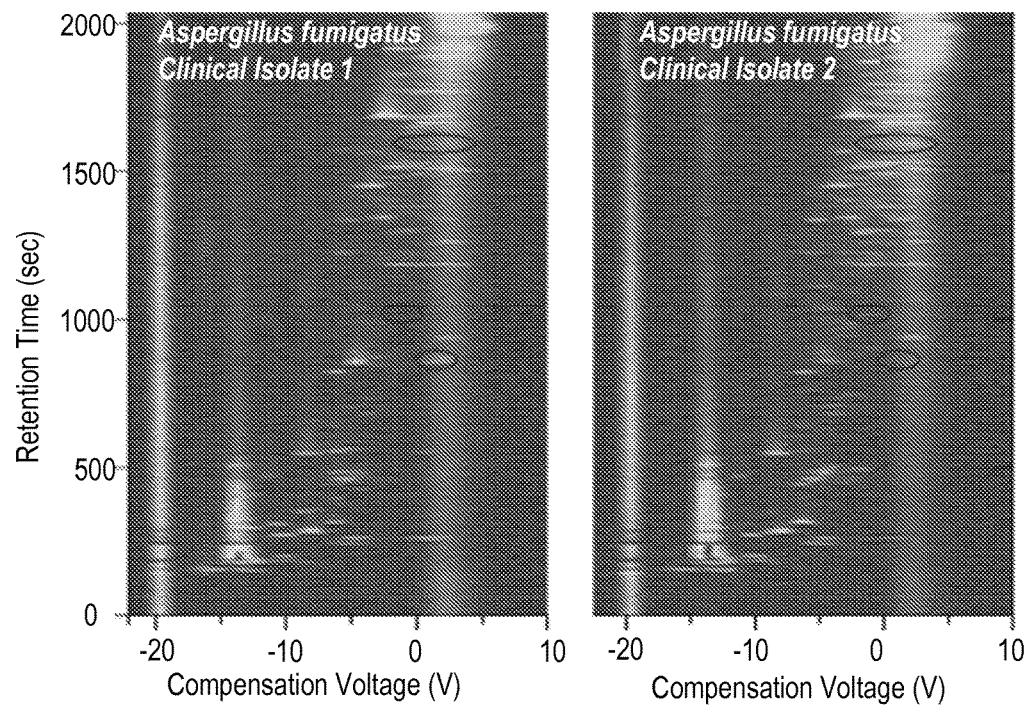
FIG. 10. Positive ion DMS spectra of *Aspergillus* species, showing A) Conservation of the DMS pattern between two members of *A. fumigatus*, and B) Conservation of the DMS pattern between two members of *A. terreus*. The DMS pattern is clearly different between *A. fumigatus* and *A. terreus*.
Figure 10B:
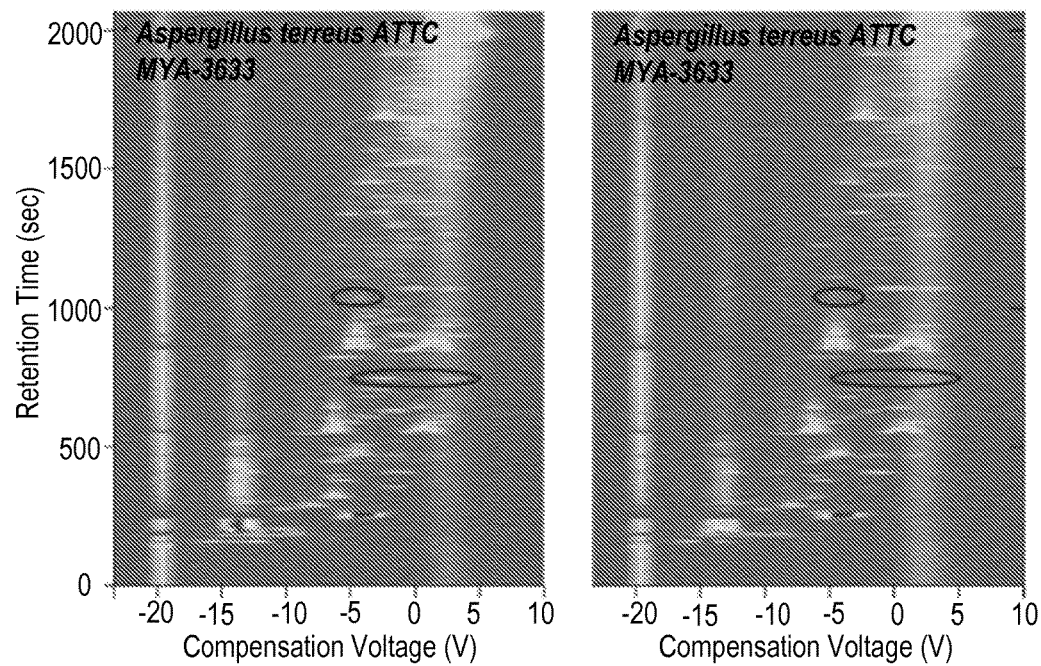

Definition of GC-Differential Mobility Spectrometer Patterns of *A. fumigatus* and *A. terreus*:

As a step towards utilizing portable GC-differential mobility spectrometry (DMS) technology as a point-of-care gas detector for *Aspergillus*, the eluent from the GC was split between a MS and a DMS device. DMS is an extremely sensitive and selective chemical detector that operates at atmospheric pressure with a small power source, allowing it to be used outside the laboratory for the detection of specific VOC patterns. DMS positive ion spectral features of headspace gas from *A. fumigatus* and *A. terreus* were examined. The DMS pattern was clearly conserved within members of each species and clearly distinct between *A. fumigatus* and *A. terreus* (FIG. 10A, 10B).

Figure 11:
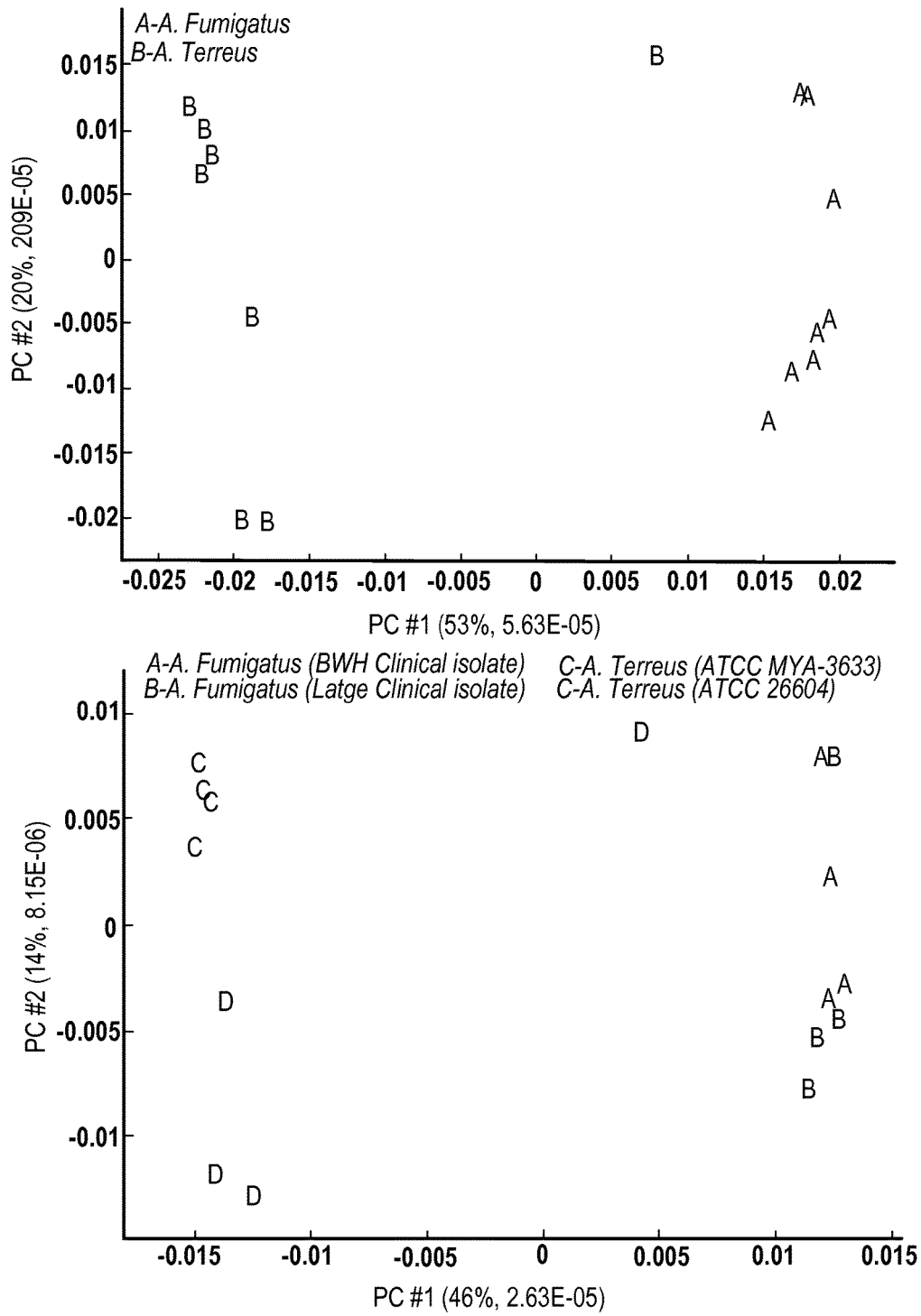
FIG. 11. Principal component analysis (PCA) score plots for *A. fumigatus* and *A. terreus*. A) Each letter represents an experimental replicate of type strains of *A. fumigatus* (A) and *A. terreus* (B). Percentage of total variance and absolute Eigenvalue are outlined in parentheses on each axis. There is clear clustering of *A. fumigatus* and *A. terreus* DMS features and separation between these species. B) Each letter represents an experimental replicate of clinical and culture collection strains of *A. fumigatus* (A, B) and *A. terreus* (C, D), with clear clustering within species and distinct separation between species.

Using principal component analysis (PCA), the degree of class separation between *A. fumigatus* and *A. terreus* was evaluated. There was clustering of samples from the same species, and clear separation between *A. fumigatus* and *A. terreus* clusters (FIG. 11A, 11B).

Detection of *A. fumigatus* VOCs in Patient Breath:

Tidal breath was collected from 54 immunocompromised patients with suspected invasive aspergillosis to assess whether patients with IA could be distinguished from patients without IA by detecting fungal VOCs in their breath.

Of 54 patients, 23 (43%) were female, 46 (85%) had a hematologic malignancy, 22 (41%) allogeneic stem cell transplants, 6 (11%) solid organ transplants, 46 (85%) exposure to T-cell immunosuppressants, and 24 (44%) prolonged neutropenia. These characteristics were comparable in 29 patients with EORTC/MSG proven (3) or probable (26) IA and 25 patients with nodular pneumonia caused by other fungal infections or other infectious processes.

Figure 12:
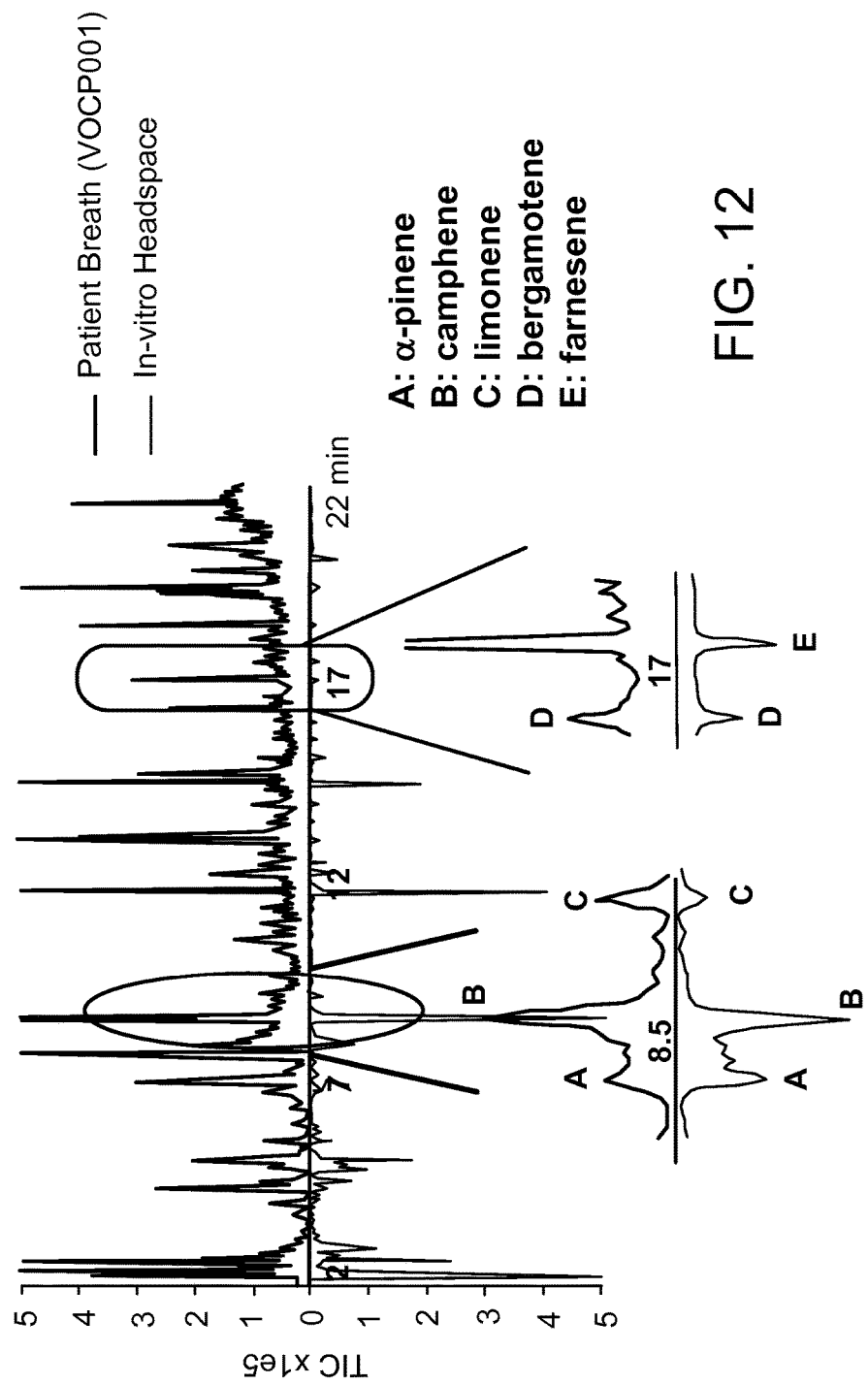
FIG. 12. Overlay of the GC-MS total ion chromatograph of a representative breath sample of a patient with invasive aspergillosis (black chromatogram) and an in vitro culture of *A. fumigatus* Af293 (inverted red chromatogram).

There was substantial overlap between the key *A. fumigatus* VOCs we identified in vitro and in the breath of patients with invasive aspergillosis (FIG. 12), although we also identified a new sesquiterpene compound, beta-vatirenene, and an oxidized farnesene derivative, cis-geranylacetone, in the breath of patients with IA that were not induced by any of our in vitro culture conditions.

Figure 13:
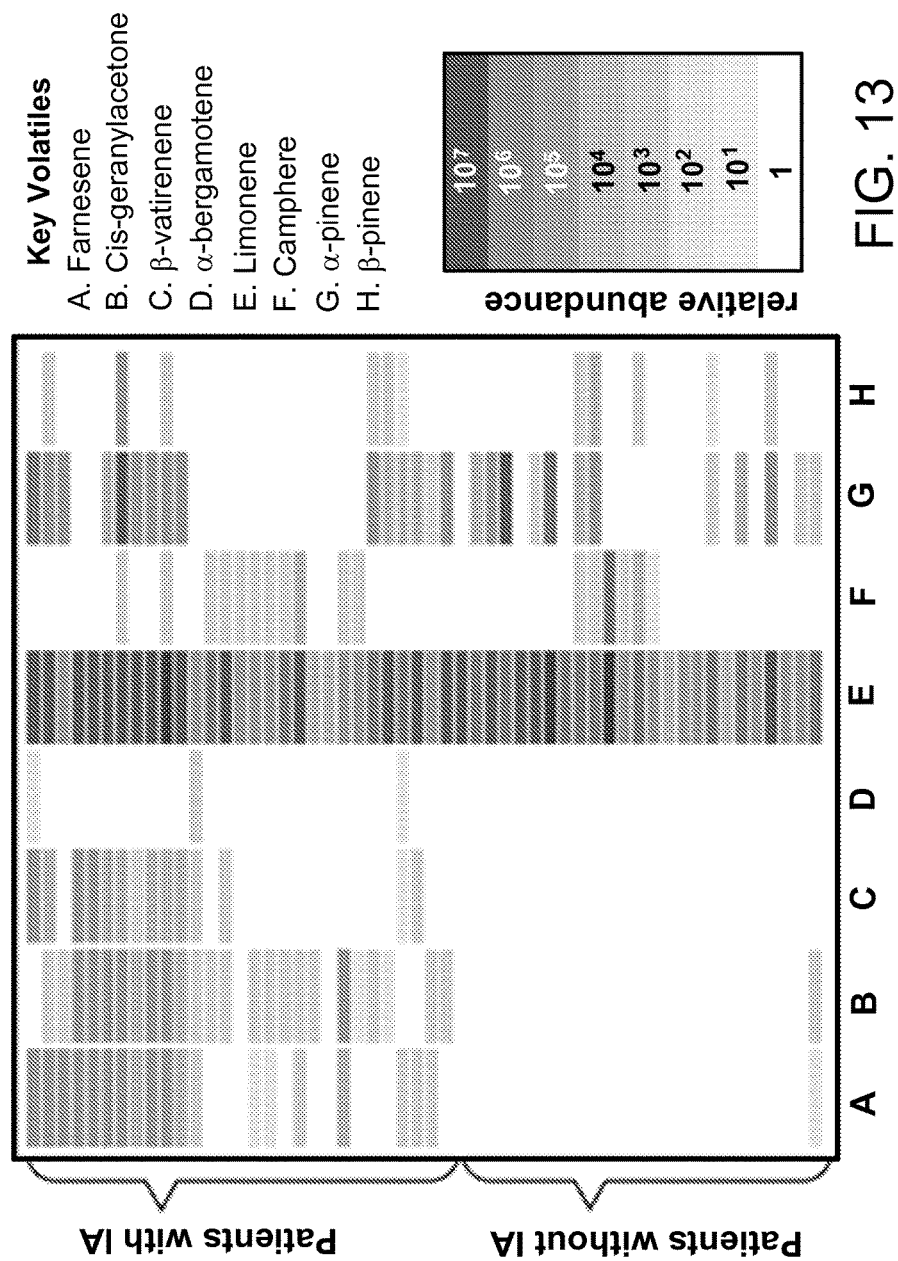
FIG. 13. Heatmap of the relative abundance of each key *A. fumigatus* VOC in the breath of patients with IA and patients without IA. Each row represents an individual patient's breath and each column represents one of the key *A. fumigatus* VOCs.
Figure 14:
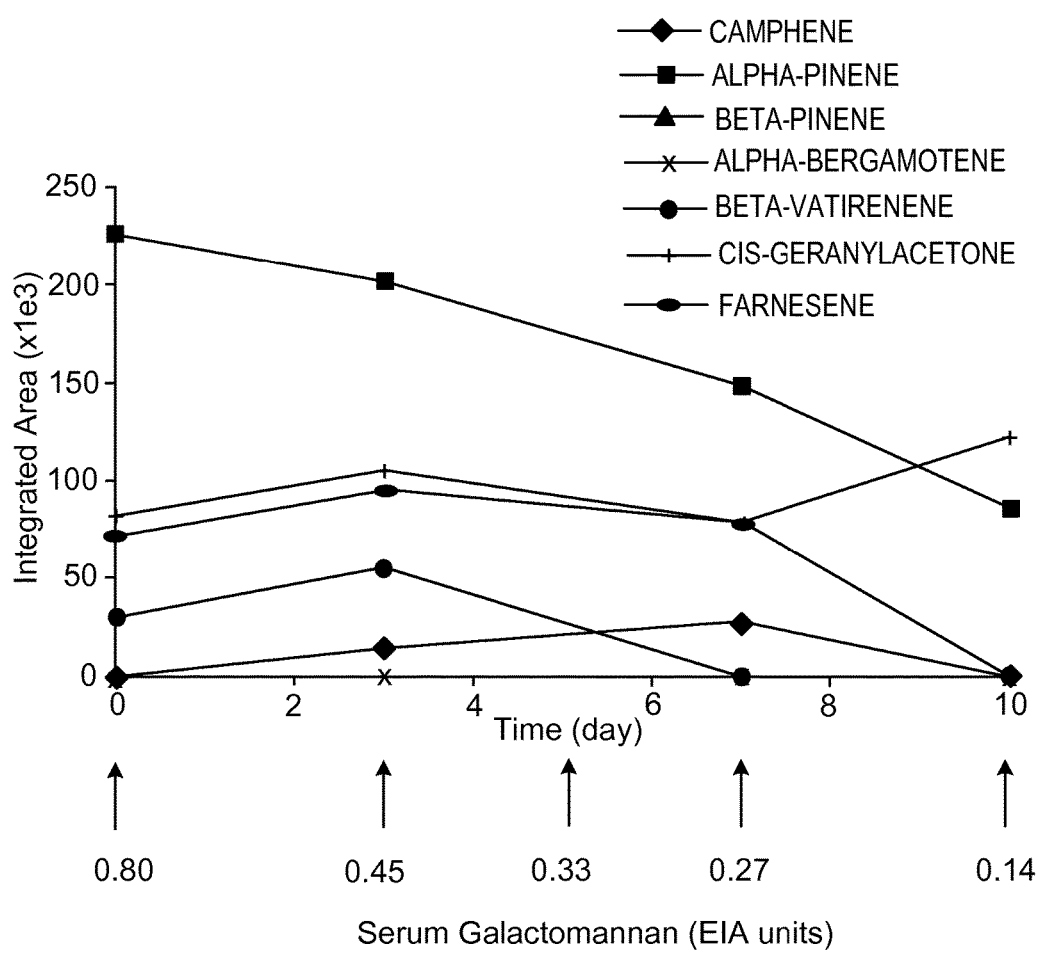
FIG. 14. Attenuation of breath *A. fumigatus* compounds with antifungal therapy.

While some of the key VOCs identified in *A. fumigatus* in vitro were present equally in patients with and without IA, a combination of the sesquiterpenes farnesene and beta-vatirenene and the oxidized farnesene derivative cis-geranylacetone distinguished patients with IA from patients without IA correctly in 51/54 (94%) patients (FIG. 13)—27 of 29 patients with IA (sensitivity=93%) and 24 or 25 patients who ultimately had other causes of pneumonia (sensitivity=96%). These VOCs were absent in ambient air control samples collected concurrently with each breath sample.

Breath was collected from a few patients serially following initiation of antifungal therapy and these key *A. fumigatus* VOCs appeared to decline over 1-2 weeks of treatment.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for diagnosing and treating a subject having invasive aspergillosis (IA), the method comprising:
   obtaining a sample comprising breath of the subject
   assaying the sample to detect the presence in the sample of one or both of beta-vatirenene and alpha-bergamotene;
      diagnosing the subject as having IA based on the presence of beta-vatirenene or alpha-bergamotene in the sample; and
   administering an antifungal treatment to the subject diagnosed as having IA.

2. A method of treating a subject who has invasive aspergillosis (IA), the method comprising:
   obtaining a sample comprising breath of the subject;
   assaying the sample to detect the presence in the sample of one or both of beta-vatirenene and alpha-bergamotene; and administering an antifungal treatment to the subject who has one or both of beta-vatirenene and alpha-bergamotene in the breath of the subject.

3. The method of claim 2, wherein the treatment comprises administration of one or more doses of one or more antifungal compounds.

4. A method of monitoring efficacy of a treatment for invasive aspergillosis (IA) in a subject, the method comprising:
assaying a first sample comprising breath from the subject to detect a first level of volatile organic compounds (VOCs) comprising one or both of beta-vatirenene and alpha-bergamotene;
administering a treatment for IA to the subject;
determining a second level of the VOCs in a second sample comprising breath from the subject obtained after administration of the treatment to the subject; and
comparing the first and second levels of VOCs, wherein a decrease in the VOCs indicates that the treatment has been effective in treating the IA in the subject, and an increase or no change indicates that the treatment has not been effective in treating the IA in the subject.

5. The method of claim 4, wherein the treatment comprises administration of one or more doses of one or more antifungal compounds.

6. The method of claim 1, wherein assaying the sample comprises using gas chromatography (GC) or spectrometry.

7. The method of claim 6, wherein the spectrometry is mobility spectrometry (IMS) or differential mobility spectrometry (DMS).

8. The method of claim 1, wherein the subject is a human.

9. The method of claim 2, wherein the subject is a human.

10. The method of claim 3, wherein the antifungal compound is amphotericin B; an azole antifungal compound; or an echinocandin antifungal compound.

11. The method of claim 2, wherein assaying the sample comprises using gas chromatography (GC) or spectrometry.

12. The method of claim 11, wherein the spectrometry is mobility spectrometry (IMS) or differential mobility spectrometry (DMS).

13. The method of claim 4, wherein assaying the sample to detect the first level or the second level of the VOCs comprises using gas chromatography (GC) or spectrometry.

14. The method of claim 13, wherein the spectrometry is mobility spectrometry (IMS) or differential mobility spectrometry (DMS).

15. The method of claim 4, wherein the subject is a human.

16. A method for diagnosing and treating a subject having invasive aspergillosis (IA), the method comprising:
obtaining a sample comprising headspace from a culture suspected of comprising *Aspergillus* isolated from the subject;
assaying the sample to detect the presence in the sample of beta-vatirenene and alpha-bergamotene;
diagnosing the subject as having IA based on the presence of beta-vatirenene and alpha-bergamotene in the sample; and
administering an antifungal treatment to the subject diagnosed as having IA.

17. The method of claim 16, wherein assaying the sample comprises using gas chromatography (GC) or spectrometry.

18. A method of treating a subject who has invasive aspergillosis (IA), the method comprising:
obtaining a sample comprising headspace from a culture suspected of comprising *Aspergillus* isolated from the subject;
assaying the sample to detect the presence in the sample of beta-vatirenene and alpha-bergamotene; and
administering an antifungal treatment to the subject who has one or both of beta-vatirenene and alpha-bergamotene in the sample comprising headspace from the culture isolated from the subject.

19. The method of claim 18, wherein the treatment comprises administration of one or more doses of one or more antifungal compounds.

20. A method of monitoring efficacy of a treatment for invasive aspergillosis (IA) in a subject, the method comprising:
assaying a first sample comprising headspace from a culture suspected of comprising *Aspergillus* isolated from the subject to detect a first level of volatile organic compounds (VOCs) comprising beta-vatirenene and alpha-bergamotene;
administering a treatment for IA to the subject;
determining a second level of the VOCs in a second sample comprising headspace from a culture suspected of comprising *Aspergillus* isolated from the subject after administration of the treatment to the subject; and
comparing the first and second levels of VOCs, wherein a decrease in the VOCs indicates that the treatment has been effective in treating the IA in the subject, and an increase or no change indicates that the treatment has not been effective in treating the IA in the subject.

21. The method of claim 1, wherein the sample is assayed to detect the presence of both beta-vatirenene and alpha-bergamotene, and the subject is diagnosed as having IA based on the presence of both beta-vatirenene and alpha-bergamotene in the sample.

22. The method of claim 2, where the sample is assayed to detect the presence of both beta-vatirenene and alpha-bergamotene, and the antifungal treatment is administered to the subject who has both beta-vatirenene and alpha-bergamotene in the breath of the subject.

23. The method of claim 4, wherein the VOCs comprise both beta-vatirenene and alpha-bergamotene.

* * * * *

UNITED STATES PATENT AND TRADEMARK OFFICE
CERTIFICATE OF CORRECTION

PATENT NO. : 10,031,125 B2
APPLICATION NO. : 14/426678
DATED : July 24, 2018
INVENTOR(S) : Sophia Koo et al.

Page 1 of 1

It is certified that error appears in the above-identified patent and that said Letters Patent is hereby corrected as shown below:

In the Claims

In Column 14, Line 53, Claim 1, delete "subject" and insert -- subject; --,

In Column 16, Line 17 (approx.), Claim 18, after "has" delete "one or".

Signed and Sealed this
Sixth Day of November, 2018

Andrei Iancu
*Director of the United States Patent and Trademark Office*

UNITED STATES PATENT AND TRADEMARK OFFICE
CERTIFICATE OF CORRECTION

PATENT NO. : 10,031,125 B2
APPLICATION NO. : 14/426678
DATED : July 24, 2018
INVENTOR(S) : Sophia Koo et al.

It is certified that error appears in the above-identified patent and that said Letters Patent is hereby corrected as shown below:

In the Specification

Column 1, Lines 13, replace "FEDERALLY SPONSORED RESEARCH OR DEVELOPMENT
This invention was made with Government support under Grants No. R21AI085454, K23AI097225 and 8UL1TR000170 awarded by the National Institutes of Health. The Government has certain rights in the invention."

With -- STATEMENT OF FEDERALLY SPONSORED RESEARCH
This invention was made with government support under Grant Nos. AI085454, and AI097225 awarded by the National Institutes of Health. The government has certain rights in the invention. --

Signed and Sealed this
Sixteenth Day of May, 2023

Katherine Kelly Vidal
*Director of the United States Patent and Trademark Office*